United States Patent
Tang et al.

(10) Patent No.: US 12,329,769 B2
(45) Date of Patent: Jun. 17, 2025

(54) USE OF ABELMOSCHI COROLLA EXTRACT IN PREPARATION OF DRUG FOR TREATING FIBROSIS

(71) Applicants: SUZHONG PHARMACEUTICAL GROUP CO., LTD., Taizhou (CN); JIANGSU SUZHONG PHARMACEUTICAL RESEARCH INSTITUTE CO., LTD., Nanjing (CN)

(72) Inventors: Haitao Tang, Taizhou (CN); Zhengyu Cao, Nanjing (CN); Boyang Yu, Nanjing (CN); Chengzhi Chai, Nanjing (CN); Haitao Ge, Taizhou (CN); Zhengjun Wang, Taizhou (CN)

(73) Assignees: SUZHONG PHARMACEUTICAL GROUP CO., LTD., Taizhou (CN); JIANGSU SUZHONG PHARMACEUTICAL RESEARCH INSTITUTE CO., LTD., Nanjing (CN)

( * ) Notice: Subject to any disclaimer, the term of this patent is extended or adjusted under 35 U.S.C. 154(b) by 833 days.

(21) Appl. No.: 17/596,413

(22) PCT Filed: May 18, 2020

(86) PCT No.: PCT/CN2020/090897
§ 371 (c)(1),
(2) Date: Dec. 9, 2021

(87) PCT Pub. No.: WO2020/248776
PCT Pub. Date: Dec. 17, 2020

(65) Prior Publication Data
US 2022/0339177 A1    Oct. 27, 2022

(30) Foreign Application Priority Data

Jun. 13, 2019 (CN) .......................... 201910509730.7
Aug. 14, 2019 (CN) .......................... 201910746618.5

(51) Int. Cl.
*A61K 31/7048* (2006.01)
*A61K 31/407* (2006.01)
*A61K 36/185* (2006.01)

(52) U.S. Cl.
CPC ........ *A61K 31/7048* (2013.01); *A61K 31/407* (2013.01); *A61K 36/185* (2013.01)

(58) Field of Classification Search
None
See application file for complete search history.

(56) References Cited

PUBLICATIONS

Billeter, M., et al., 8-Hydroxyflavonoid glucuronides from Malva Sylvestris, Phytochemistry, 30 (Dec. 1991) pp. 987-990. (Year : 1991).*
Yi, Z., et al., Isolation and identification of chemical constituents from the flowers of *Abelmoschus manihot*(L.) Medic(III), J. Shenyang Pharm. Univ., 28 (Jul. 31, 2011) pp. 520-525. (Year: 2011).*

* cited by examiner

*Primary Examiner* — Dominic Lazaro
(74) *Attorney, Agent, or Firm* — CBM PATENT CONSULTING, LLC

(57) ABSTRACT

Provided is the use of an *Abelmoschi corolla* extract in the preparation of a drug for treating fibrosis, wherein the extract contains at least 15% of gossypetin-3-O-β-D-glucose-8-O-β-D-glucuronide, with same being prepared by means of the following method: taking medicinal materials of *Abelmoschi corolla*, heating same with ethanol and performing reflux extraction, performing filtration, concentrating the filtrate, and carrying out macroporous resin column chromatography, where same is firstly washed with water, then eluting same with 3-7% of ethanol, eluting same with 9-15% of ethanol, and collecting 9-15% of an ethanol eluent in order to obtain the *Abelmoschi corolla* extract.

17 Claims, 4 Drawing Sheets

USE OF ABELMOSCHI COROLLA EXTRACT IN PREPARATION OF DRUG FOR TREATING FIBROSIS

TECHNICAL FIELD

The present invention belongs to the field of medicines, and more particularly, relates to use of an *Abelmoschi corolla* extract in preparation of a drug for treating fibrosis.

BACKGROUND

*Abelmoschi corolla* is the dried corolla of *Abelmoschus Manihot* (L.) Medic, which is a plant of *Abelmoschus* in Malvaceae. The *Abelmoschi corolla* was first recorded in Materia Medica of Jia You Reign. The *Abelmoschi corolla* is widely distributed and rich in resources. According to the records in Compendium of Materia Medica, the flower smells sweet, is cold and smooth and non-toxic, is mainly used to treat stranguria and hasten parturition. For those with malignant sores and pus for a long time, they should be immediately healed after being applied with *Abelmoschi corolla* powder. Therefore, the *Abelmoschi corolla* is an important drug for treating sores, and eliminating gangrene and swelling, and treat burn injury by immersing the flower in oil and then coating. In modern medicine, the main effective constituent of the *Abelmoschi corolla* is a flavonoid constituent. At present, researches on chemical constituents also focus on the total flavone of A (TFA) and the monomer thereof. These researches prove that the TFA can reduce proteinuria, relieve erythrocyte urine, alleviate tubulointerstitial lesions, eliminate oxygen free radicals, improve erythrocyte immune adhesion, promote the transport and clearance of a human circulating immune complex (CIC), regulate a cellular immune function, and inhibit a humoral immune response, thus alleviating a kidney injury mediated by the human circulating immune complex (CIC), improving a renal function, and achieving a purpose of treating a chronic kidney disease (CKD).

Huangkui Capsule has been sold in the market for nearly 20 years, and has a good clinical effect in treating the chronic kidney disease. There have been documentary records that an *Abelmoschus manihot* extract has a certain therapeutic effect on renal fibrosis; however, it is still not clear what kinds of extract constituent and corresponding monomer constituent are.

Flavonoid compounds are widely found in natural plants, and gossypetin and gossypin are typical representatives of hexahydroxy flavonoid compounds. The gossypetin is mainly present in plants of *Hibiscus*, such as *Hibiscus sabdariffa*. The gossypin is a product of replacing an 8-hydroxyl of the gossypetin by glucose, and is widely found in plants of Malvaceae, such as *Abelmoschus* manihot, Hibiseu manihot, *Hibiscus* vitifolius, *Abelmoschus esculentus, Abutilon indicum*, and the like.

SUMMARY

One object of the present invention is to provide use of an *Abelmoschi corolla* extract in preparation of a drug for treating fibrosis. The extract includes at least 15% of gossypetin-3-O-β-D-glucose-8-O-β-D-glucuronide by weight. Further preferably, the extract includes at least 15% of gossypetin-3-O-β-D-glucose-8-O-β-D-glucuronide by weight and includes acortatarin A.

A content of the gossypetin-3-O-β-D-glucose-8-O-β-D-glucuronide is 20% to 95% by weight, preferably 30% to 80%, and further preferably 40% to 70%.

The fibrosis includes, but is not limited to pulmonary fibrosis, liver fibrosis and renal fibrosis, is preferably the renal fibrosis, and is further preferably diabetic renal fibrosis.

Further, the above *Abelmoschi corolla* extract is prepared by the following method: taking medicinal materials of *Abelmoschi corolla*, carrying out ethanol heating reflux extraction, filtering, concentrating the filtrate, carrying out macroporous resin column chromatography, washing the column with water first, eluting the column with 3% to 7% ethanol, then eluting the column with 9% to 15% ethanol, and collecting the 9% to 15% ethanol eluate to obtain the *Abelmoschi corolla* extract; the ethanol in the ethanol heating reflux is preferably 50% to 95% ethanol, and further preferably 80% to 95% ethanol; and the eluting the column with 9% to 15% ethanol is preferably eluting the column with 10% ethanol.

Further, in the preparation method of the present invention, the macroporous resin column chromatography sequentially includes: washing the column with water, eluting the column with 5% ethanol and eluting the column with 10% ethanol, wherein an elution dosage for gradient elution of each solvent is preferably 3 bed volumes to 7 bed volumes.

Further, the *Abelmoschi corolla* extract is prepared by the following method: carrying out reflux extraction on the medicinal materials of *Abelmoschi corolla* with 85% to 95% ethanol for one to three times, with each time lasting for one to two hours, filtering, combining filtrates and recovering ethanol, concentrating the filtrate to a specific gravity of 1.20 to 1.35, standing the concentrated solution at 0° C. to 4° C. for 24 hours to 48 hours to obtain a refrigerated solution, removing an oil layer of the refrigerated solution, adjusting the pH value to 6.0 to 7.0, concentrating, carrying out D101 macroporous resin column chromatography, eluting the column with 5 bed volumes of pure water, 5 bed volumes of 5% ethanol and 7 bed volumes of 10% ethanol sequentially, and collecting a 10% ethanol elution fraction.

Another object of the present invention is to provide an *Abelmoschi corolla* extract, which includes at least 15% of gossypetin-3-O-β-D-glucose-8-O-β-D-glucuronide by weight, preferably 20% to 95%, more preferably 30% to 80%, and further preferably 40% to 70%; and further preferably includes acortatarin A.

A third object of the present invention is to provide use of gossypetin-3-O-β-D-glucose-8-O-β-D-glucuronide in preparation of a drug for treating fibrosis. The fibrosis is pulmonary fibrosis, liver fibrosis and renal fibrosis, especially renal fibrosis related to a chronic kidney disease; and is further preferably renal fibrosis related to diabetic nephropathy.

A fourth object of the present invention is to provide use of an *Abelmoschi corolla* extract in preparation of a drug for treating renal fibrosis, wherein the *Abelmoschi corolla* extract is also called 15% ethanol eluate, and is prepared by the following method of: taking medicinal materials of *Abelmoschi corolla*, carrying out ethanol heating reflux extraction, filtering, concentrating the filtrate, carrying out macroporous resin column chromatography, washing the column with water, eluting the column with 5% ethanol, eluting the column with 10% ethanol and eluting the column with 15% ethanol sequentially, and collecting the 15% ethanol eluate and concentrating to obtain the *Abelmoschi corolla* extract; and the ethanol in the ethanol heating reflux is preferably 50% to 95% ethanol, and more preferably 80% to 95% ethanol. The elution dosage in gradient elution of each solvent is preferably 3 bed volumes to 7 bed volumes.

A fifth object of the present invention is to provide an extract of plant, which includes at least 15% of gossypetin-3-O-β-D-glucose-8-O-β-D-glucuronide by weight. Preferably, the extract of plant includes 20% to 95% gossypetin-3-O-β-D-glucose-8-O-β-D-glucuronide by weight, preferably 30% to 80%, and further preferably 40% to 70%.

The plant is a plant of *Hibiscus* and a plant of Malvaceae, and further preferably one or more of *Hibiscus sabdariffa*, *Abelmoschus* manihot, Hibiseu manihot, *Hibiscus* vitifolius, *Abelmoschus esculentus*, and *Abutilon indicum*.

The *Abelmoschi corolla* extract of the present invention has an excellent anti-fibrosis effect, especially an excellent anti-diabetic renal fibrosis effect. Especially, 10% ethanol eluate has more significant therapeutic activity than other elution fractions.

The gossypetin-3-O-β-D-glucose-8-O-β-D-glucuronide of the present invention has an excellent anti-fibrosis effect, especially an excellent anti-diabetic renal fibrosis effect, is a monomer compound with an optimal anti-fibrosis activity in the *Abelmoschi corolla* so far, and is more remarkable than quercetin.

DETAILED DESCRIPTION

The contents of the present invention are further described hereinafter with reference to the accompanying drawings.

Embodiment 1: Preparation of Abelmoschi Corolla Extract

Specification 6,000 g of medicinal materials of *Abelmoschi corolla* were taken, subjected to reflux extraction twice with 15 times (mass/volume ratio) of 95% ethanol, with each time lasting for one hour, and then filtered. The filtrates were combined and the ethanol was recovered, then the filtrate was concentrated to a specific gravity of 1.20, the concentrated solution was stood at 0° C. to 4° C. for 24 hours, and an oil layer of a refrigerated solution was removed. A pH value was adjusted to 6.0, and the solution was slowly added into a vacuum band drier after concentration, dried, crushed, and packed into a clean double-layer plastic bag, thus obtaining the *Abelmoschi corolla* extract, which was also called a 95% ethanol extract of *Abelmoschi corolla*.

A content of hyperin in the extract was 1.6% by weight. A content of water in the extract was no more than 10% by weight.

Embodiment 2: Preparation of Abelmoschi Corolla Extract 3,000 g of medicinal materials of *Abelmoschi corolla* were taken, subjected to reflux extraction twice with 19 times of 95% ethanol, with each time lasting for one hour, and then filtered. The filtrates were combined and the ethanol was recovered, then the filtrate was concentrated to a specific gravity of 1.20, the concentrated solution was stood at 0° C. to 4° C. for 48 hours, and an oil layer of a refrigerated solution was removed. A pH value was adjusted to 6.0, and the solution was slowly added into a vacuum band drier after concentration, dried at 100° C., crushed, and packed into a clean double-layer plastic bag, thus obtaining the *Abelmoschi corolla* extract, which was also called a 95% ethanol extract.

A content of hyperin in the extract was about 1.5% to 1.9% by weight. A content of water in the extract was no more than 10% by weight.

Embodiment 3: Establishment of Fingerprint Spectrum of Abelmoschi Corolla Extract 13 batches of samples of the *Abelmoschi corolla* extract prepared by the method in Embodiment 1 were taken to establish the fingerprint spectrum.

Chromatographic condition of fingerprint spectrum: chromatographic column: Agilent, ZORBAX SB-C18 (4.6 mm×250 mm, 5 μm). Mobile phases: A phase, 0.1% phosphoric acid-water; and C phase, acetonitrile. Gradient elution was carried out according to a mobile phase gradient elution procedure in Table 1. Flow rate: 1.0 mL/min. Sample introduction amount: 10 μL. Column temperature: 35° C. Detection wavelength: 254 nm.

TABLE 1

| Mobile phase gradient elution procedure | | |
|---|---|---|
| Time (min) | Acetonitrile (%) | 0.1% phosphoric acid solution (%) |
| 0 | 6 | 94 |
| 20 | 17 | 83 |
| 30 | 17 | 83 |
| 50 | 40 | 60 |
| 55 | 6 | 94 |
| 60 | 6 | 94 |

Figure 1:
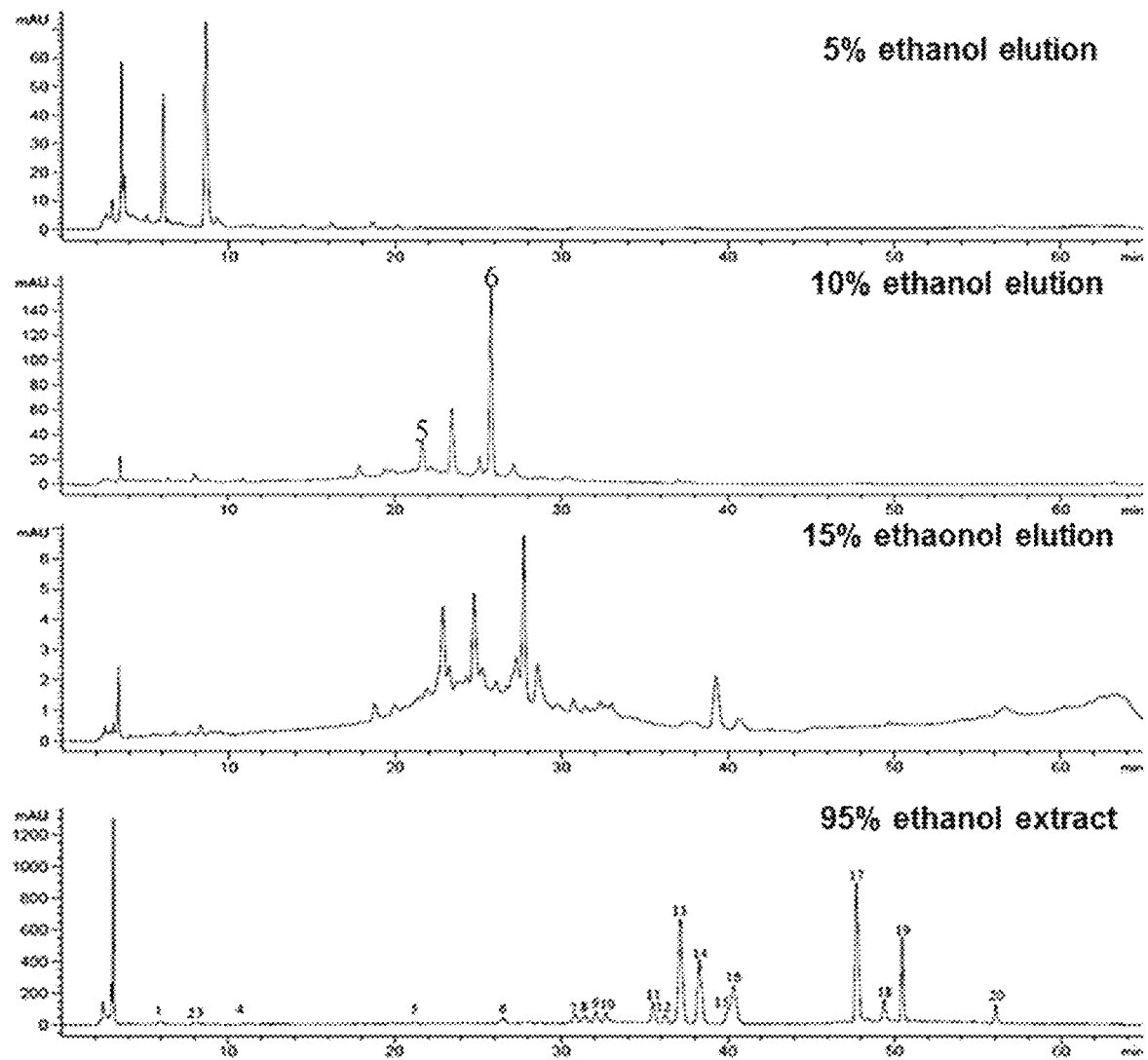
FIG. 1 shows fingerprint spectra of 95% ethanol extract of *Abelmoschi corolla* and each ethanol elution fraction of macroporous resin.

The fingerprint spectrum of the *Abelmoschi corolla* extract refers to the part of "95% ethanol extract" in FIG. 1, wherein a mass ratio of a compound 6 is no more than 1.3%.

Embodiment 4: Enrichment of Gradient Elution Constituent of Macroporous Resin of Abelmoschi Corolla Extract and Confirmation of Monomer Constituent 24 g of *Abelmoschi corolla* extract prepared by the method in Embodiment 1 was taken, a macroporous resin column (D101) had a length of 48 cm and an inner diameter of 5 cm. Samples was loaded by a dry method, and the samples had a height of 5.5 cm. The samples were sequentially eluted with pure water, 5% ethanol, 10% ethanol, 15% ethanol, 20% ethanol, 25% ethanol, 30% ethanol, 35% ethanol and 50% ethanol, wherein 5 column volumes to 7 column volumes of samples were eluted in each gradient. Fractions with the same gradient were combined, concentrated under a reduced pressure, heated in water bath and dried.

Extracts of elution fractions of macroporous resin were prepared respectively, including a water eluate, a 5% ethanol eluate, a 10% ethanol eluate, a 15% ethanol eluate, a 20% ethanol eluate, a 25% ethanol eluate, a 30% ethanol eluate, a 35% ethanol eluate and a 50% ethanol eluate.

A fingerprint spectrum test was carried out on each elution fraction of macroporous resin to determine a main monomer constituent included in the extract of each elution fraction.

HPLC fingerprint spectrum conditions were: chromatographic column: Agilent, ZORBAX SB-C18 (4.6 mm×250 mm, 5 μm). Mobile phases: A phase: 0.1% phosphoric acid-water; and C phase: acetonitrile. An elution condition is shown in Table 1. Flow rate: 1.0 mL/min; sample introduction amount: 10 μL; column temperature: 35° C.; and detection wavelength: 254 nm. Refer to FIG. 1 for specific spectrum.

In the fingerprint spectra of the *Abelmoschi corolla* extract and each elution fraction of macroporous resin, 20 fingerprint spectrum peaks were pointed out, and 20 compounds were identified. In the fingerprint spectra of the ethanol elution fractions of macroporous resin, two peaks of a 10% ethanol elution fraction were pointed out as a peak 5 (acortatarin A) and a peak 6 (gossypetin-3-O-β-D-glucose-8-O-β-D-glucuronide) respectively by comparison with a standard substance according to mass spectrometric data and nuclear magnetic data, and the gossypetin-3-O-β-D-glucose-8-O-β-D-glucuronide was not detected in other elution fractions, such as 20%, 30% or 50% ethanol elution fractions.

A yield of each elution fraction is shown in Table 2:

TABLE 2

Yield of each elution fraction

| Elution gradient | Elution volume (BV) | Mass (g) |
| --- | --- | --- |
| 5% ethanol | 5 | 1.1774 |
| 10% ethanol | 7 | 1.0177 |
| 15% ethanol | 5 | 0.4886 |
| 20% ethanol | 7 | 0.9887 |
| 25% ethanol | 7 | 1.5652 |
| 30% ethanol | 7 | 1.7990 |
| 35% ethanol | 7 | 1.5585 |
| 50% ethanol | 5 | 0.9910 |

Confirmation of each monomer constituent is shown in Table 3:

TABLE 3

Confirmation of each monomer constituent

| Peak number | Compound |
| --- | --- |
| 1 | Gallic acid |
| 2 | 5-hydroxymethyl-2-furoic acid |
| 3 | Protocatechuic acid-3-O-β-D-glucoside |
| 4 | Protocatechuic acid |
| 5 | acortatarin A |
| 6 | Gossypetin-3-O-β-D-glucose-8-O-β-D-glucuronide |
| 7 | Quercetin-3-O-[β-D-xylosyl (1→2)-α-L-rhamnosyl (1→6)-β-D-galactoside |
| 8 | Myricetin-3-O-β-D-galactoside |

TABLE 3-continued

Confirmation of each monomer constituent

| Peak number | Compound |
| --- | --- |
| 9 | Myricetin-3-O-β-D-glucoside |
| 10 | Quercetin-3-O-β-D-xylosyl-(1→2)-β-D-galactoside |
| 11 | Quercetin-3-O-robibioside |
| 12 | Rutin |
| 13 | Hyperin |
| 14 | Isoquercetin |
| 15 | Myricetin-3'-O-β-D-glucoside |
| 16 | Gossypetin-3'-O-β-D-glucoside |
| 17 | Gossypetin-8-O-β-D-glucuronide |
| 18 | Myricetin |
| 19 | Quercetin-3'-O-β-D-glucoside |
| 20 | Quercetin |

A content of gossypetin-3-O-β-D-glucose-8-O-β-D-glucuronide of the 10% ethanol elution fraction is 31%.

Embodiment 5 Effects of Each Elution Fraction of Macroporous Resin and Monomer Constituent on Activity of NRK-49F Cells NRK-49F cells were inoculated into a 96-well plate at a density of $5 \times 10^3$ cells/well, and cultured in a DMEM medium containing 10% fetal bovine serum for 16 hours. 50 μg/mL gradient elution constituent solution of macroporous resin of an *Abelmoschi corolla* extract or 30 μM of monomer constituents of the *Abelmoschi corolla* extract were added. After co-incubation for 24 hours, an original culture solution was removed, and 100 μL of 0.5 mg/mL MTT was added into each well. After incubation in an incubator for 4 hours, a staining solution was removed, and 150 μL of DMSO was added for detection by a microplate reader.

It can be seen from results of MTT that a 5% ethanol elution fraction of macroporous resin of the *Abelmoschi corolla* extract and a monomer compound 18 can significantly inhibit the activity of the NRK-49F cells. Other constituents and monomer compounds have no significant effect on the activity of the NRK-49F cells.

Embodiment 6 In-Vitro Anti-Fibrosis Effects of Abelmoschi Corolla Extract Constituent and Monomer Constituent NRK-49F cells were inoculated into a 6-well plate at a density of $5 \times 10^5$ cells/well, and cultured in a DMEM medium containing 10% fetal bovine serum for 16 hours. After adding 50 μg/mL *Abelmoschi corolla* extract and each elution fraction constituent of macroporous resin and 30 μM monomer constituent of *Abelmoschus manihot* for 30 minutes, 10 mg/mL TGF-β1 was added. After co-incubation for 24 hours, cell proteins were extracted for a WB experiment to detect expression of Collagen I and α-SMA proteins, so as to judge the in-vitro anti-fibrosis effects of the *Abelmoschi corolla* extract and each elution constituent of macroporous resin and the monomer constituent.

Figure 2:
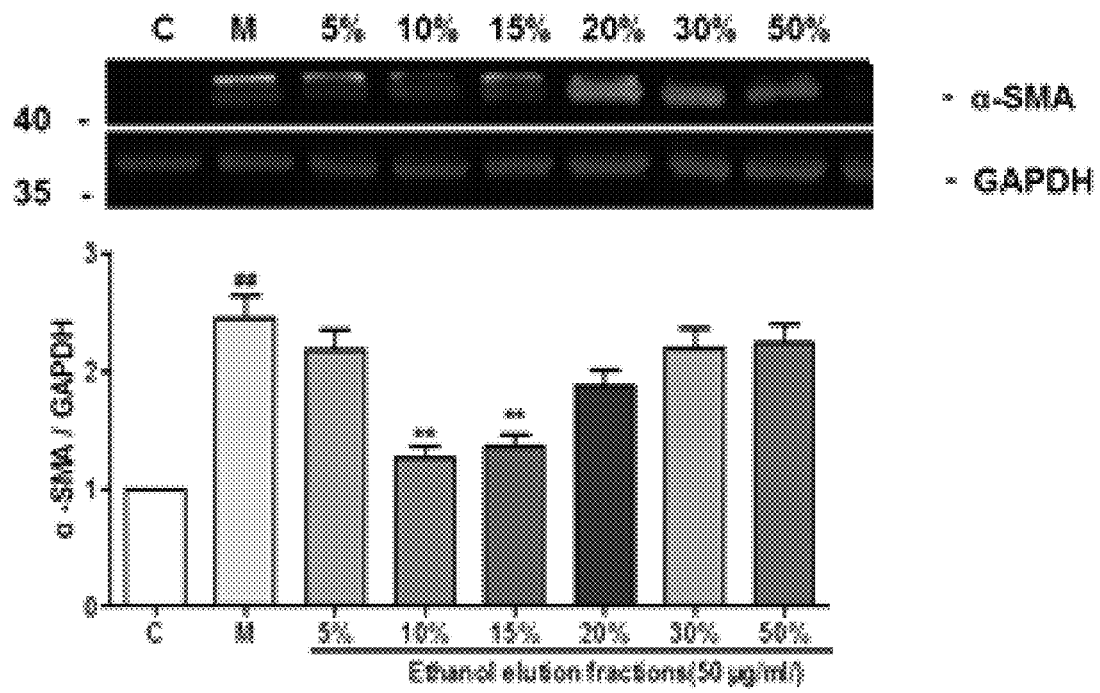
FIG. 2 shows an effect of each ethanol elution fraction of the macroporous resin of the 95% ethanol extract of the *Abelmoschi corolla* on fibrosis of NRK-49F cells stimulated by TGF-β1.
Figure 3:
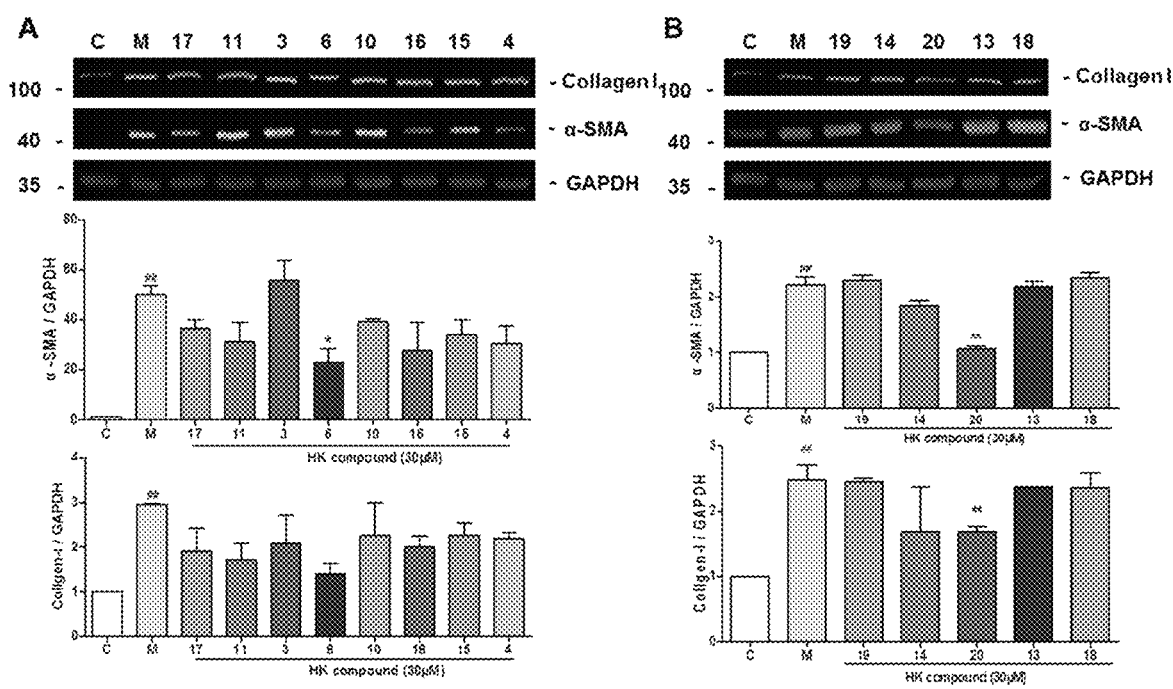
FIG. 3 shows an effect of each monomer constituent of each ethanol elution fraction of the macroporous resin of the 95% ethanol extract of the *Abelmoschi corolla* on fibrosis of NRK-49F cells stimulated by TGF-β1.
Figure 4:
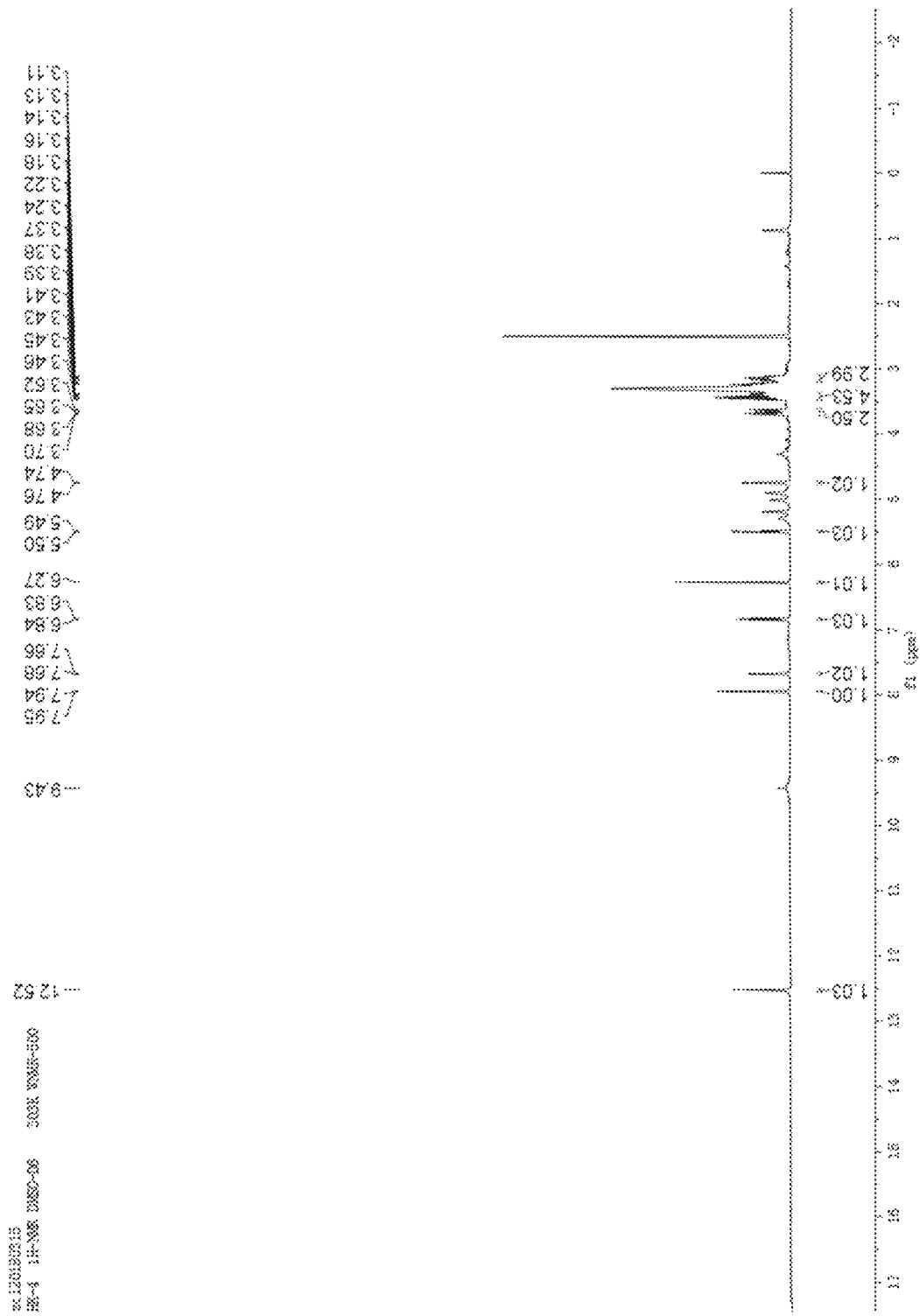
FIG. 4 is a 1H-NMR spectrum of a compound 6 (gossypetin-3-O-β-D-glucose-8-O-β-D-glucuronide).
Figure 5:
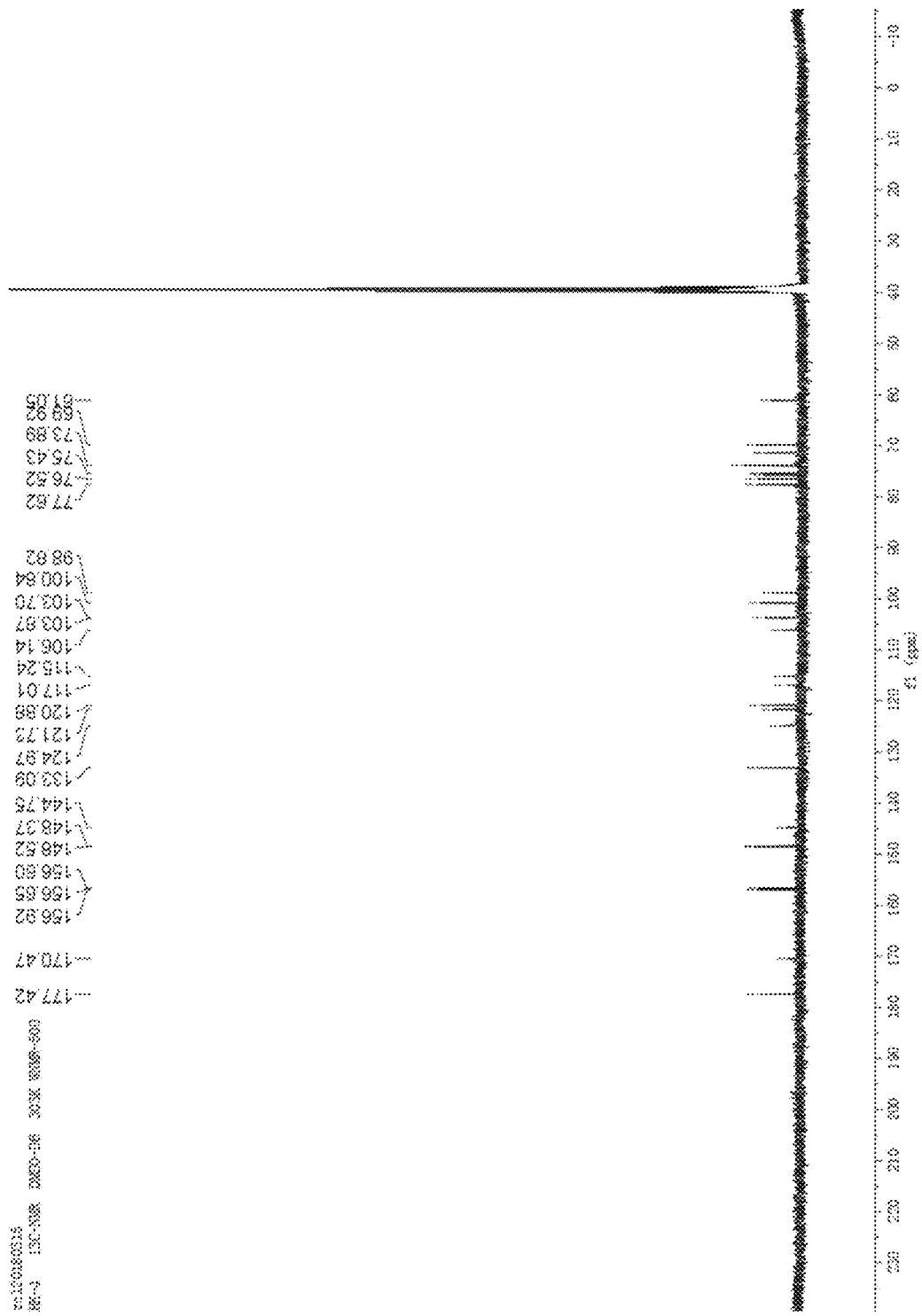
FIG. 5 is a 13C-NMR spectrum of the compound 6 (gossypetin-3-O-β-D-glucose-8-O-β-D-glucuronide).

In a model of fibrosis of NRK-49F cells stimulated by TGF-β1, a 10% ethanol elution fraction and a 15% ethanol elution fraction of macroporous resin of the *Abelmoschi corolla* extract could significantly reduce expression of the fibrosis-related protein α-SMA, as shown in FIG. 2. In an experiment of an *Abelmoschi corolla* monomer compound, a compound 6 (gossypetin-3-O-β-D-glucose-8-O-β-D-glucuronide) and a compound 20 (quercetin) could significantly inhibit the expression of the Collagen I and α-SMA proteins, as shown in FIG. 3. It can be seen from results in FIG. 1 that the 10% ethanol elution fraction of the *Abelmoschus manihot* extract mainly includes the compound 6, so that the anti-fibrosis effects of the *Abelmoschi corolla* extract constituent and the monomer constituent are further confirmed. A 1H-NMR spectrum and a 13C-NMR spectrum of the compound 6 (gossypetin-3-O-β-D-glucose-8-O-β-D-glucuronide) are respectively shown in FIG. 4 and FIG. 5.

The above detailed description is the specific description of one of the feasible embodiments of the present invention, and the embodiment is not intended to limit the patent scope of the present invention. All equivalent implementations or changes without departing from the present invention shall be included in the scope of the technical solution of the present invention.

What is claimed is:

1. An herbal extract for treating fibrosis comprising at least 15% of gossypetin-3-O-β-D-glucose-8-O-β-D-glucuronide and acortatarin A by weight, wherein the herbal extract is prepared by the following steps: taking an herbal, carrying out ethanol heating reflux extraction of the herbal, filtering, concentrating a filtrate, carrying out macroporous resin column chromatography, washing the column with water first, then eluting the column with 3% to 7% ethanol, then eluting the column with 9% to 15% ethanol, and collecting a 9% to 15% ethanol eluate in order to obtain the herbal extract; wherein the ethanol is 50% to 95% in the step of ethanol heating reflux extraction.

2. The herbal extract according to claim 1, wherein the herbal extract comprises 20% to 95% of gossypetin-3-O-β-D-glucose-8-O-β-D-glucuronide and acortatarin A by weight; wherein the herbal is a *Hibiscus* or a Malvaceae.

3. The herbal extract according to claim 2, wherein the herbal extract is prepared as a drug for treating fibrosis; wherein the herbal extract is extracted from abelmoschi corolla, and comprises at least 15% of gossypetin-3-O-β-D-glucose-8-O-β-D-glucuronide and acortatarin A by weight; wherein the abelmoschi corolla is a dried corolla of *Abelmoschus* Manihot.

4. The herbal extract according to claim 3, wherein the herbal extract comprises 20% to 95% of gossypetin-3-O-β-D-glucose-8-O-β-D-glucuronide and acortatarin A by weight.

5. The herbal extract according to claim 3, wherein the ethanol is 80% to 95% in the step of ethanol heating reflux extraction; and the ethanol is 10% in the step of the eluting the column with 9% to 15% ethanol.

6. The herbal extract according to claim 2, wherein the herbal extract comprises 30% to 80% of gossypetin-3-O-β-D-glucose-8-O-β-D-glucuronide and acortatarin A by weight; wherein the herbal is one or more selected from the group consisting of *Abelmoschus* manihot, Hibiseu manihot, *Hibiscus* vitifolius, *Abelmoschus esculentus* and *Abutilon indicum*.

7. The herbal extract according to claim 6, wherein the herbal extract comprising 40% to 70% of gossypetin-3-O-β-D-glucose-8-O-β-D-glucuronide and acortatarin A by weight.

8. The herbal extract according to claim 4, wherein the herbal extract comprises 40% to 70% of gossypetin-3-O-β-D-glucose-8-O-β-D-glucuronide and acortatarin A by weight.

9. The herbal extract according to claim 1, wherein the fibrosis is selected from the group consisting of pulmonary fibrosis, liver fibrosis and renal fibrosis, wherein the renal fibrosis is from chronic kidney disease or diabetic nephropathy.

10. The herbal extract according to claim 1, wherein the macroporous resin column chromatography sequentially comprises: washing the column with water, eluting the column with 5% ethanol, and eluting the column with 10% ethanol, wherein an elution dosage for gradient elution of each solvent is 3 bed volumes to 7 bed volumes.

11. The herbal extract according to claim 1, wherein the herbal extract is prepared by the following steps: carrying out reflux extraction on abelmoschi corolla with 85% to 95% ethanol for one to three times, with each time lasting for one to two hours, filtering, combining filtrates and recovering ethanol, concentrating the filtrate to a specific gravity of 1.20 to 1.35, standing the concentrated solution at 0° C. to 4° C. for 24 hours to 48 hours to obtain a refrigerated solution, removing an oil layer of the refrigerated solution, adjusting the pH value to 6.0 to 7.0, concentrating, carrying out macroporous resin column chromatography by eluting the column with 5 bed volumes of pure water, 5 bed volumes of 5% ethanol and 7 bed volumes of 10% ethanol sequentially, and collecting a 10% ethanol elution fraction in order to obtain the herbal extract.

12. An abelmoschi corolla extract for treating renal fibrosis, comprising at least 15% of gossypetin-3-O-β-D-glucose-8-O-β-D-glucuronide and acortatarin A by weight; wherein the abelmoschi corolla extract is prepared by the following method: taking abelmoschi corolla, carrying out ethanol heating reflux extraction, filtering, concentrating the filtrate, carrying out macroporous resin column chromatography, washing the column with water, eluting the column with 5% ethanol, eluting the column with 10% ethanol, and eluting the column with 15% ethanol sequentially, and collecting 15% ethanol eluate and concentrating to obtain the abelmoschi corolla extract; wherein the abelmoschi corolla is a dried corolla of *Abelmoschus* Manihot.

13. The abelmoschi corolla extract according to claim 12, wherein the ethanol is 50% to 95% in the step of the ethanol heating reflux.

14. The abelmoschi corolla extract according to claim 12, wherein the abelmoschi corolla extract comprises 20% to 95% of gossypetin-3-O-β-D-glucose-8-O-β-D-glucuronide and acortatarin A by weight.

15. The abelmoschi corolla extract according to claim 14, wherein the abelmoschi corolla extract comprises 40% to 70% of gossypetin-3-O-β-D-glucose-8-O-β-D-glucuronide and acortatarin A by weight.

16. The abelmoschi corolla extract according to claim 13, wherein the ethanol is 80% to 95% in the step of the ethanol heating reflux.

17. The abelmoschi corolla extract according to claim 12, wherein the fibrosis is selected from the group consisting of pulmonary fibrosis, liver fibrosis and renal fibrosis, wherein the renal fibrosis is from chronic kidney disease or diabetic nephropathy.

* * * * *